(12) United States Patent
Singh et al.

(10) Patent No.: US 12,138,242 B1
(45) Date of Patent: Nov. 12, 2024

(54) CONTROLLING NEUROPATHIC PAIN

(71) Applicant: Frimline Private Limited, Gujarat (IN)

(72) Inventors: Ankit Shyam Singh, Gujarat (IN);
Vedprakash Mishra, Gujarat (IN);
Neelima Tongra, Rajasthan (IN)

(73) Assignee: Frimline Private Limited, Ahmedabad Gujarat (IN)

( * ) Notice: Subject to any disclaimer, the term of this patent is extended or adjusted under 35 U.S.C. 154(b) by 0 days.

(21) Appl. No.: 18/302,975

(22) Filed: Apr. 19, 2023

Related U.S. Application Data

(63) Continuation of application No. 15/923,079, filed on Mar. 16, 2018, now abandoned.

(30) Foreign Application Priority Data

Jul. 5, 2017 (IN) .............................. 201721023668

(51) Int. Cl.
*A61K 31/352* (2006.01)
*A61K 31/164* (2006.01)
*A61K 31/215* (2006.01)
*A61P 25/02* (2006.01)
*A61P 25/04* (2006.01)

(52) U.S. Cl.
CPC .......... *A61K 31/352* (2013.01); *A61K 31/164* (2013.01); *A61K 31/215* (2013.01); *A61P 25/02* (2018.01); *A61P 25/04* (2018.01)

(58) Field of Classification Search
None
See application file for complete search history.

(56) References Cited

U.S. PATENT DOCUMENTS

| | | | |
|---|---|---|---|
| 5,506,224 | A | 4/1996 | Della Valle et al. |
| 5,990,170 | A | 11/1999 | Della Valle et al. |
| 2004/0157932 | A1 | 8/2004 | Saebo |
| 2008/0089845 | A1 | 4/2008 | Compton et al. |
| 2008/0269325 | A1 | 10/2008 | Rice et al. |
| 2011/0112181 | A1 | 5/2011 | Kweon et al. |

FOREIGN PATENT DOCUMENTS

| | | |
|---|---|---|
| EP | 1082292 B1 | 9/2005 |
| EP | 2444078 A1 | 4/2012 |
| EP | 2944309 A1 | 11/2015 |
| EP | 3130336 A1 | 2/2017 |
| NL | 2011448 C | 3/2014 |
| WO | WO 2001/010434 A1 | 2/2001 |
| WO | WO 2001/024645 A1 | 4/2001 |
| WO | WO 2002/080860 A2 | 10/2002 |
| WO | WO 2005/046580 A2 | 5/2005 |
| WO | WO 2008/100977 A2 | 8/2008 |
| WO | WO 2011/027373 A1 | 3/2011 |
| WO | WO 2012/015704 A2 | 2/2012 |
| WO | WO 2013/028570 A2 | 2/2013 |
| WO | WO 2013/121449 A1 | 8/2013 |
| WO | WO 2014/017936 A2 | 1/2014 |
| WO | WO 2015/007613 A1 | 1/2015 |
| WO | WO 2015/007615 A1 | 1/2015 |
| WO | WO 2015/012708 A1 | 1/2015 |
| WO | WO 2015/016728 A1 | 2/2015 |
| WO | WO 2015/157313 A1 | 10/2015 |
| WO | WO 2016/063217 A1 | 4/2016 |
| WO | WO 2016/146453 A1 | 9/2016 |
| WO | WO 2016/183184 A1 | 11/2016 |
| WO | WO 2016/185468 A1 | 11/2016 |
| WO | WO 2016/193905 A1 | 12/2016 |

OTHER PUBLICATIONS

Emanuela Esposito et al.; Palmitoylethanolamide in Homeostatic and Traumatic Central Nervous System Injuries:; CNS & Neurological Disoders—Drug Targets; No. 12; 2013; pp. 55-61.

Jan M. Keppel Hesselink et al.; "Therapeutic utility of palmitoylethanolamide in the treatment of neuropathic pain associated with various pathological conditions a case series"; Journal of Pain Research; No. 5; 2012; pp. 437-442.

Giampiero Colombano et al.; "O-(Triazolyl) methyl carbamates as a novel and potent class of fatty acid amide hydrolase (FAAH) inhibitors"; Chem Med Chem 0000; Wiley Online Library; pp. 1-17.

Katerina Otrubova et al.; "The discovery and development of inhibitors of fatty acid amide hydrolase (FAAH)"; Bioorganic & Medicinal Chemistry Letters; No. 21; 2011; pp. 4674-4685.

Michael Eddleston et al.; "Implications of the BIA-102474-101 study for review of first-into-human clinical trials"; British Journal of Clinical Pharmacology; No. 81; pp. 582-586.

Christophe Mallet et al.; "FAAH inhibitors in the limelight, but regrettably"; International Journal of Clinical Pharmacology and Therapeutics; vol. 54; No. 7; 2016; pp. 498-501.

Rimplejeet Kaur et al.; "What failed BIA 10-2474 Phase I clinical trial? Global speculations and recommendations for future Phase I trials"; Journal of Pharmacology and Pharmacotherapeutics; Jul.-Sep. 2016; vol. 7; Issue 3; pp. 120-126.

Cocito D. et al., Pain Research and Treatment 14, Article ID 854560, May 2014.

(Continued)

*Primary Examiner* — David J Blanchard
*Assistant Examiner* — Daniel F Coughlin
(74) *Attorney, Agent, or Firm* — BakerHostetler

(57) ABSTRACT

The present application describes a method of treating neuropathic pain in a patient. The method includes a step of administering a pharmaceutical composition to the patient. The pharmaceutical composition consists of one or more pharmaceutically acceptable excipients, Palmitoylethanolamide (PEA) ranging from 35 to 80% by weight, one or more naturally occurring Fatty Acid Amide Hydrolase (FAAH) Inhibitors ranging from 0.5 to 40% by weight, and optionally a vitamin and/or a co-enzyme. The combination of PEA and the one or more naturally occurring FAAH inhibitors in the administered pharmaceutical composition act synergistically to reduce neuropathic pain in the patient.

4 Claims, No Drawings

CONTROLLING NEUROPATHIC PAIN

CROSS-REFERENCE TO RELATED APPLICATION

This application is a continuation of U.S. patent application Ser. No. 15/923,079, filed Mar. 16, 2018, entitled "Controlling Neuropathic Pain," which claims priority to Indian Patent Application No. 201721023668, filed Jul. 5, 2017, the entire contents of each application are hereby incorporated by reference herein.

FIELD OF THE INVENTION

The present invention relates to controlling neuropathic pain. More particularly, the invention relates to controlling neuropathic pain by administering a composition/formulation comprising a synergistic combination of Palmitoylethanolamide (PEA) and one or more natural ingredients.

BACKGROUND OF THE INVENTION

Humans and animals suffering from chronic and severe pain require good clinical management. Multiple pharmacological agents are generally employed to treat diverse pathological pain states. Specifically, these pharmacological agents include opiates, nonsteroidal antiinflammatory drugs, anticonvulsants, antidepressants, ketamine and others (Guindon et al., 2007). However, adverse side effects from these pharmacological agents constrain therapeutic dosing ultimately limiting therapeutic efficacy.

Improvements have been made in understanding pathophysiological mechanisms underlying chronic pain states. In addition, efforts have been made in developing different analgesic mechanisms for chronic pain that are not only effective, but also nontoxic and devoid of unwanted central side effects. Further improvements in chronic pain management are still required.

Neuropathic pain (NP) is one such chronic pain, which needs good clinical management. Neuropathic pain is defined as a pain that comes from problems with signals from the nerves. Neuropathic pain is different from the common type of pain caused by an injury, burn, pressure, etc. Indeed, neuropathic pain results from damage to or dysfunction of the peripheral or central nervous system, rather than stimulation of pain receptors. Diagnosis is suggested by out of proportion pain to tissue injury, dysesthesia (e.g., burning, tingling), and signs of nerve injury detected during neurologic examination. While different therapies have been suggested for treating and managing Neuropathic pain, one therapy in particular suggests employing Palmitoylethanolamide (PEA). PEA is an endogenous, fatty acid amide food component first discovered in the late 1950s when it was shown that the anti-allergic and anti-inflammatory activity exerted by egg yolk, peanut oil or soybean lecithin was due to a specific lipid fraction corresponding to PEA (Esposito and Cuzzocrea, 2013). PEA, was used many decades ago in some countries, but due to a lack of insight in its mechanism of action, interest weaned. Since the 1990s, interest surged again due to the discovery of its effects in many different animal paradigms for pain and chronic inflammation (J Pain Res. 2012; 5: 437-442). PEA is synthesized and metabolized by different animal cell types and is also present in herbs or plants. It exerts a multitude of physiological functions related to metabolic and cellular homeostasis. It is a key element in the regulation of pathways linked to the inflammation process particularly in the down-regulation of the mastocytes degranulation process, and processes underlying itching and pain.

Cannabinoid-based medicines have therapeutic potential for the treatment of pain. Augmentation of levels of endocannabinoids with inhibitors of fatty acid amide hydrolase (FAAH) is analgesic. FAAH is a membrane-bound serine hydrolase that belongs to the amidase signature family of hydrolases. FAAH enzyme breaks down fatty acid amides such as anandamide (N-arachidonoylethanolamide), N-oleoylethanolamide (N-OEA), PEA and oleanide. FAAH belongs to a large and diverse class of enzymes referred to as the amidase signature (AS) family.

FAAH Inhibitors are a class of molecules that inactivate the FAAH Enzymes by preventing the hydrolysis of anandamide, oleoylethanolamide and PEA. It thereby increases endogenous levels. Known chemically synthesized FAAH inhibitors are BIA 10-2474, URB524, URB-597, URB694, URB937, etc. These inhibitors are disclosed in the article published by Colombano et al. titled, "O-(Triazolyl) methyl carbamates as a novel and potent class of fatty acid amide hydrolase (FAAH) inhibitors" and in the article published by Otrubova et al. titled, "The discovery and development of inhibitors of fatty acid amide hydrolase (FAAH)."

RELATED PRIOR ARTS

U.S. Pat. No. 5,990,170 discloses a method of synthesis of PEA.

U.S. Pat. No. 5,506,224 refers to a method for treating diseases involving mast cell degranulation, as a consequence of a neurogenic and/or immunogenic hyper-stimulation, comprising the administration of an effective amount of a series of compounds included in a general formula, comprising also the PEA.

EP1082292 discloses a composition comprising anandamide and PEA.

WO 2001/010434 describes a pharmaceutical composition comprising PEA in micronized form having particle size less than 10 µm for use in the veterinary field.

WO 2001/024645 discloses a nutritional or therapeutic composition for oral administration, which comprises a naturally occurring precursor that is metabolized to a compound having anandamide activity for use as a medicament, in which such precursor is a long chain polyunsaturated fatty acid (LCPUFA) (e.g. arachidonic acid ARA or docosahexaenoic acid DIA) or a derivative thereof having a given general formula. According to an embodiment reported in such application, the composition also comprises an inhibitor of an anandanide inactivating enzyme (amidase), which is said to include PEA. However, no biological effects or further technical results of such hypothetical combination comprising PEA have been shown in such document.

WO 2002/080860 and WO 2005/046580 refers to a method of reducing food intake or reducing appetite in a mammal, said method comprising orally administering a fatty acid alkanolamide compound, derivative, homolog, or analog. PEA is reported to be one of such fatty acid alkanolamide compounds.

WO 2011/027373 A1 discloses a pharmaceutical composition containing an ultra-micronized form of PEA, in which more than 90% by weight of PEA has particle sizes lower than 6 microns (mm).

NL2011448 discloses a pharmaceutical composition comprising PEA particles and/or pharmaceutically acceptable esters or salts thereof, in which the PEA particles are substantially free of pharmaceutical excipients.

WO 2013/121449 discloses a use of chemically synthesized FAAH/NAAH inhibitor in association with oxazoline of PEA, for a combined, separate or sequential administration.

EP2444078 describes the activity of PEA and other Aliamides in the treatment of renal diseases. Silymarin is an extract of the plant *Silybum marianum*, also known as milk thistle, the activity of which in the treatment of liver diseases is known.

EP2944309 and WO 2016/185468 disclose a pharmaceutical composition comprising a combination of PEA and Opioid use for the treatment of pain.

WO 2016/063217 discloses a combination of PEA and *Spirulina* for the treatment of inflammatory states.

WO 2016/146453 discloses a pharmaceutical composition comprising a combination of PEA and a vitamin B.

WO 2016/183134 provides compositions comprising PEA, and an anti-inflammatory or anti-pain component.

WO 2016/193905 discloses a pharmaceutical composition comprising a combination of PEA and lycopene, and/or pharmaceutically acceptable salts and/or derivatives thereof.

EP3130336 relates to a food and/or nutraceutical composition comprising PEA. In particular, it relates to a food and/or nutraceutical composition comprising PEA in association with at least one component selected from a second active ingredient and an agent that modifies its release in the organism.

There are several patent applications (WO 2012/015704, WO 2013/028570, WO 2014/017936, WO 2015/07613, WO 2015/07615, WO 2015/012708, WO 2015/016728, WO 2015/157313), which disclose chemically synthesized different types of FAAH inhibitors which elevate PEA level. However, these chemically synthesized FAAH inhibitors may have side effects upon administration in human or animals. Several studies reveal the serious side-effects (including death) of chemically synthesized FAAH inhibitors. Some of them include Eddleston Michael et al; "Implications of the BIA-102474-101 study for review of first-into-human clinical trials", Br J Clin Pharmacol (2016) 81 582-586; Mallet et. al.; "FAAH inhibitors in the limelight, but regrettably", International Journal of Clinical Pharmacology and Therapeutics, Vol. 54—No. 7/2016 (498-501); and Kaur et al." "What failed BIA 10-2474 Phase I clinical trial? Global speculations and recommendations for future Phase I trials", J Pharmacol Pharmacotherapy. 2016 July-September; 7(3): 120-126.

Current treatment options for neuropathic pain mainly focus on neuronal system suppressing GABA or other inhibitory receptors. Most of the drugs used for neuropathic pain cause drowsiness, dizziness, blurred vision, somnolence, peripheral edema, psychomotor slowing and paresthesia and many more. These side effects decrease the Quality of Life of patient and reduce active working life. Also, these drugs require dosage adjustment in different disease conditions such as renal disease or liver disease etc. Moreover using these drugs for long-term causes de-sensitization of receptors. Therefore, the requirement of increase in the dose of these drugs is required to elicit the desired response and that leads to more number of side effects. In conclusion, the current treatment paradigm has some gaps and requires some new arsenal to fight against Neuropathic Pain.

The above-mentioned documents disclosing use of FAAH inhibitors are chemically synthesized, and there can be side effects due to synthetic ingredients. Hence, there is a requirement to develop formulations, which use natural ingredients, including natural FAAH inhibitors. Further, there is also requirement to provide a highly effective relief for neuropathic pain by PEA and its combination with other active ingredients without any side effects in humans or animals accompanied with good tolerability at an effective dose and good safety profile. Hence, there exists a need for combinations of PEA, which are highly effective in a neuropathic pain, accompanied by acceptable safety profile and without any adverse effects.

SUMMARY OF THE INVENTION

The present application provides a pharmaceutical composition/formulation comprising a synergistic combination of Palmitoylethanolamide (PEA) and one or more naturally occurring Fatty Acid Amide Hydrolase (FAAH) Inhibitor. In a preferred aspect, the present invention provides a composition or formulation comprising a synergistic combination of Palmitoylethanolamide and at least two naturally occurring FAAH inhibitors.

In another aspect, the present invention provides a pharmaceutical composition/formulation comprising a synergistic combination of Palmitoylethanolamide (PEA) and one or more naturally occurring FAAH Inhibitors along with a pharmaceutically acceptable excipient.

In a further aspect, the pharmaceutical composition/formulation of the present invention additionally comprises vitamins, coenzymes or a combination thereof.

In one aspect, the natural FAAH Inhibitors in the present invention are selected from Myricetin, Isorhamnetin, Kaempferol, Pristimerin, Biochanin A, Genistein, Daidzein or a combination thereof.

In yet a further aspect, in the composition/formulation of the present invention, vitamins are selected from methylcobalamin, cyanocobalamin, benfotiamine or a combination thereof. The co-enzymes in the present invention are selected from ubidecarenone, thiamine pyrophosphate, Flavin adenine dinucleotide or a combination thereof.

In even another aspect, the pharmaceutical composition/formulation of the present invention comprises a synergistic combination of PEA, Daidzein, Genistein and a pharmaceutically acceptable excipient.

In another aspect of the present application, a process for the preparation of a composition/formulation is described. The process comprises (a) weighing and sieving the ingredients through a suitable sieve, (b) mixing the ingredients, (c) preparing a dough by adding a binder solution to the mixed ingredients and sieving to obtain granules, (d) drying the granules till the level of dryness (LOD) is reduced to less than 1.5% w/w to obtain semi dried granules, and (e) sieving the semi dried granules through a suitable sieve to obtain the composition/formulation. The process further comprises adding lubricants or glidants to the semi-dried granules and filling the granules in Hydroxypropylmethyl cellulose (HPMC) capsule shells and sealing.

In a preferred aspect, the application provides a process for preparing the composition/formulation of the present invention. The process comprises sifting previously weighed PEA, Natural FAAH Inhibitor(s), diluent(s), and disintegrating agent(s) separately through a sieve, mixing the contents to obtain a mixture, preparing a binder solution, and optionally adding second natural FAAH Inhibitor(s) in to the binder solution, adding the binder solution to the mixture obtained above and obtaining granules, drying the obtained granules to obtain semi dried granules and sifting the semi dried granules through a sieve, sifting previously weighed Lubricant(s) or glidant(s) separately through a sieve and mixing with the sifted semi dried granules to obtain a blend of the composition/formulation. The blend is further filled and sealed with HPMC capsule shells.

DETAILED DESCRIPTION OF THE INVENTION

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected along with the present pharmaceutical carriers. Further, the responses may vary depending upon the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

An objective of the present invention is to provide a composition/formulation comprising a synergistic combination of PEA and one or more natural ingredients.

In an embodiment, the present application provides a composition/formulation comprising a synergistic combination of PEA with at least one of a naturally occurring FAAH Inhibitor. In one aspect, the composition/formulation of the present invention may optionally comprise vitamins and coenzymes. The composition/formulation of the present invention is able to provide a safe composition/formulation of PEA with one or more natural ingredients with enhanced or synergistic effects compared to PEA alone in the treatment of neuropathic pain.

Another object of the present invention is to provide a composition/formulation comprising a synergistic combination of PEA along with at least one of a naturally occurring FAAH Inhibitor to avoid side effects associated with synthetic FAAH inhibitors.

Another object of the present invention is to provide a composition/formulation comprising a synergistic combination of PEA along with at least one of a naturally occurring FAAH Inhibitor, and other active ingredients selected from vitamins, coenzymes or a combination thereof.

In one preferred embodiment, a composition/formulation comprising PEA in micronized or non-micronized form is described. The composition/formulation includes at least one of a naturally occurring FAAH Inhibitor. The composition/formulation optionally includes vitamins or co-enzymes.

In a preferred aspect, the present invention provides a pharmaceutical composition/formulation for treatment of neuropathic pain, wherein said composition/formulation comprises a synergistic combination of PEA with at least one of a naturally occurring FAAH inhibitor and a pharmaceutically acceptable excipient. The said composition/formulation optionally comprises vitamins or co-enzymes.

In a preferred aspect, the ratio of PEA:Natural FAAH Inhibitors is in a range of 99:1 to 50:50. In a more preferred aspect, the ratio of PEA:FAAH Inhibitor is 84:15.

The pharmaceutical composition/formulation of the present invention comprises PEA in micronized or non-micronized form. The amount of PEA in the pharmaceutical composition/formulation of the present invention ranges from 35% by wt. to 80% by wt. of the composition/formulation. In an embodiment the amount of PEA ranges from 45 to 80% by weight. In another embodiment, the amount of PEA ranges from 50 to 80% by weight. In yet another embodiment, the amount of PEA ranges from 60 to 80% by weight. In yet another embodiment, the amount of PEA ranges from 65 to 80% by weight. In yet even another embodiment, the amount of PEA ranges from 70 to 80% by weight. In yet a further embodiment the amount of PEA ranges from 75 to 80% by weight.

In a preferred embodiment, the pharmaceutical composition/formulation of the present invention comprises PEA in micronized or non-micronized form, wherein the amount of PEA in the pharmaceutical composition/formulation ranges from 150 mg to 2400 mg per unit dose.

The pharmaceutical composition/formulation of the present invention comprises at least one natural FAAH Inhibitor selected from Myricetin, Isorhamnetin, Kaempferol, Pristimerin, Biochanin A, Genistein, Daidzein. The amount of natural FAAH Inhibitor in the pharmaceutical composition/formulation of the present invention ranges from 0.5% by wt. to 40% by wt. of the composition/formulation. In an embodiment, the amount of natural FAAH Inhibitor ranges from about 1 to 40% by weight. In an embodiment, the amount of natural FAAH Inhibitor ranges from about 10 to 40% by weight. In an embodiment, the amount of natural FAAH Inhibitor ranges from about 20 to 40% by weight. In a further embodiment, the amount of natural FAAH Inhibitor ranges from about 30 to 40% by weight.

In a preferred embodiment, the pharmaceutical composition/formulation of the invention comprises at least one natural FAAH Inhibitors selected from Myricetin, Isorhamnetin, Kaempferol, Pristimerin, Biochanin A, Genistein, Daidzein, wherein the amount of natural FAAH Inhibitor in the pharmaceutical composition/formulation ranges from 2 mg to 2722 mg per unit dose.

The pharmaceutical composition/formulation of the invention optionally comprises vitamins, co-enzymes or a combination thereof.

The vitamins are selected from methylcobalamin, cyanocobalamin, benfotiamine or a combination thereof. The amount of vitamins in the pharmaceutical composition/formulation of the present invention ranges from 0.01% by wt. to 30% by wt. of the composition/formulation. The amount of vitamins in the pharmaceutical composition/formulation of the present invention ranges from 0.1 mg to 200 mg per unit dose.

The co-enzymes are selected from ubidecarenone, thiamine pyrophosphate, flavin adenine dinucleotide or a combination thereof. The amount of co-enzymes in the pharmaceutical composition/formulation of the present invention ranges from 10% by wt. to 40% by wt. of the composition/formulation. The amount of co-enzymes in the pharmaceutical composition/formulation of the present invention ranges from 50 mg to 200 mg per unit dose.

The pharmaceutical composition/formulation of the present invention can be formulated as tablets, capsules, granules, powder, sachets, suspension, solution, modified release formulations, topical formulations, etc.

The formulations of the present invention comprise suitable excipients such as diluents, disintegrants, binders, solubilizing agent, lubricants, glidants, solvents etc.

The diluents are selected from microcrystalline cellulose, lactose (anhydrous/monohydrate/spray dried), starch, cellulose powder, silicified microcrystalline, ammonium alginate, calcium carbonate, calcium lactate, dibasic calcium phosphate (anhydrous/dibasic dehydrate/tribasic), calcium silicate, calcium sulfate, cellulose acetate, compressible sugar, confectioner's sugar, corn starch, pregelatinized starch, dextrates, dextrin, dextrose, erythritol, ethylcellulose, fructose, fumaric acid, glyceryl palmitostearate, isomalt, kaolin, lactitol, magnesium carbonate, magnesium oxide, maltodextrin, maltose, mannitol, medium-chain triglycerides, polydextrose, polymethacrylates, simethicone, sodium alginate, sodium chloride, sorbitol, sterilizable maize, sucrose, sugar spheres, sulfobutylether β-cyclodextrin, talc, tragacanth, trehalose, xylitol or the like. The amount of diluent in the pharmaceutical composition/formulation of the present invention ranges from 5% by wt. to 50% by wt. of the composition/formulation.

The disintegrating agent is selected from croscarmellose sodium, crospovidone, carboxymethyl cellulose (sodium/calcium), sodium starch glycolate, alginic acid, calcium alginate, cellulose powdered, chitosan, colloidal silicon dioxide, corn starch, docusate sodium, glycine, guar gum, hydroxypropyl cellulose low-substituted, magnesium aluminum silicate, methylcellulose, microcrystalline cellulose, polacrilin potassium, povidone, sodium alginate, pregelatinized starch or the like. The amount of disintegrating agent in the pharmaceutical composition/formulation of the present invention ranges from 0.5% by wt. to 10% by wt. of the composition/formulation.

The binder is selected from hypromellose, starch, acacia, agar, alginic acid, calcium carbonate, calcium lactate, carbomers, carboxymethylcellulose sodium, carrageenan, cellulose acetate phthalate, *ceratonia*, chitosan, copovidone, corn starch, pregelatinized starch, cottonseed oil, dextrates, dextrin, dextrose, ethylcellulose, gelatin, glyceryl behenate, guar gum, hydrogenated vegetable oil type I, hydroxyethyl cellulose, hydroxyethylmethyl cellulose, hydroxypropyl cellulose, inulin, lactose, liquid glucose, low-substituted Hypromellose, magnesium aluminum silicate, maltodextrin, maltose, methylcellulose, microcrystalline cellulose, pectin, poloxamer, polycarbophil, polydextrose, polyethylene oxide, polymethacrylates, povidone, sodium alginate, stearic acid, sucrose, sunflower oil, tricaprylin, vitamin E polyethylene glycol succinate, zein or the like. The amount of binder in the pharmaceutical composition/formulation of the present invention ranges from 0.1% by wt. to 10% by wt. of the composition/formulation.

The solubilizing agent is selected from polysorbate 80, sodium lauryl sulfate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E polyethylene glycol succinate, microcrystalline cellulose, carboxymethylcellulose sodium, diethanolamine, ethylene glycol palmitostearate, glycerin monostearate, hypromellose, hypromellose acetate succinate, lecithin, polyethylene alkyl ethers, aluminum oxide, poly(methylvinyl ether/maleic anhydride), calcium carbonate, crospovidone, cyclodextrins, fructose, hydroxypropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether b-cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like. The amount of Solubilizing Agent in the pharmaceutical composition/formulation of the present invention ranges from 0.25% by wt. to 15% by wt. of the composition/formulation.

The lubricant is selected from magnesium stearate, zinc stearate, calcium stearate, glycerin monostearate, glyceryl behenate, glyceryl palmitostearate, hydrogenated castor oil, hydrogenated vegetable oil type I, light mineral oil, magnesium lauryl sulfate, medium-chain triglycerides, mineral oil, myristic acid, palmitic acid, poloxamer, polyethylene glycol, sodium benzoate, sodium chloride, sodium lauryl sulfate, sodium stearyl fumarate, stearic acid, talc, potassium benzoate or the like. The amount of Lubricant in the pharmaceutical composition/formulation of the present invention ranges from 1% by wt. to 10% by wt. of the composition/formulation.

The glidant is selected from Colloidal silicon dioxide, talc, calcium phosphate tribasic, cellulose powdered, hydrophobic colloidal silica, magnesium oxide, magnesium silicate, magnesium trisilicate, silicon dioxide or the like. The amount of Glidant in the pharmaceutical composition/formulation of the present invention ranges from 1% by wt. to 10% by wt. of the composition/formulation.

The solvent is selected from water, alcohol, isopropyl alcohol, propylene glycol, almond oil, benzyl alcohol, benzyl benzoate, butylene glycol, carbon dioxide, castor oil, corn oil (maize), cottonseed oil, dibutyl phthalate, diethyl phthalate, dimethyl ether, albumin, dimethyl phthalate, dimethyl sulfoxide, dimethylacetamide, ethyl acetate, ethyl lactate, ethyl oleate, glycerin, glycofurol, isopropyl myristate, isopropyl palmitate, light mineral oil, medium-chain triglycerides, methyl lactate, mineral oil, monoethanolamine, octyldodecanol, olive oil, peanut oil, polyethylene glycol, polyoxyl 35 castor oil, propylene carbonate, pyrrolidone, safflower oil, sesame oil, soybean oil, sunflower oil, triacetin, tricaprylin, triethanolaamine, triethyl citrate, triolein, water-miscible solvents or the like. The amount of solvent in the pharmaceutical composition/formulation of the present invention is used in a quantity sufficient.

In a preferred embodiment, the pharmaceutical composition/formulation is formulated for oral administration. Specifically, the solid pharmaceutical compositions, for example, can be in the form of tablets, capsules, pills, hard capsules filled with liquids or solids, soft capsules, sachets, powders, granules, suspensions, solutions or modified release formulations.

Developing pharmaceutical compositions or formulations wherein one or more ingredients are obtained from natural sources poses challenges for the formulator. Such challenges include providing a suitable size dosage form containing the effective amount of the active ingredients. Challenges also include providing stable formulations while retaining desirable pharmacokinetic properties. As currently understood, synthetic FAAH Inhibitors are not approved for therapeutic use in any country by any drug regulatory authority. The present invention provides stable and therapeutically effective compositions and formulations comprising PEA and one or more natural ingredients.

Some of the exemplary compositions/formulations of the present invention are described below:

Composition/Formulation 1:

| S. No. | Ingredient | Amount (% w/w) |
|---|---|---|
| 1. | PEA | 35 to 80 |
| 2. | One Natural FAAH Inhibitor | 0.5 to 40 |

Composition/Formulation 2:

| S. No. | Ingredient | Amount (% w/w) |
|---|---|---|
| 1. | PEA | 35 to 80 |
| 2. | Two Natural FAAH Inhibitors | 0.5 to 40 |

Composition/Formulation 3:

| S. No. | Ingredient | Amount (% w/w) |
|---|---|---|
| 1. | PEA | 35 to 80 |
| 2. | Natural FAAH Inhibitor(s) | 0.5 to 40 |
| 3. | Vitamin | 0.01 to 30 |

Composition/Formulation 4:

| S. No. | Ingredient | Amount (% w/w) |
|---|---|---|
| 1. | PEA | 35 to 80 |
| 2. | Natural FAAH Inhibitor(s) | 0.5 to 40 |
| 3. | Co-enzyme | 10 to 40 |

Composition/Formulation 5:

| S. No. | Ingredient | Amount (% w/w) |
|---|---|---|
| 1. | PEA | 35 to 80 |
| 2. | Natural FAAH Inhibitor(s) | 0.5 to 40 |
| 3. | Vitamin | 0.01 to 30 |
| 4 | Co-enzyme | 10 to 40 |

Composition/Formulation 6:

| S. No. | Ingredient | Amount (% w/w) |
|---|---|---|
| 1. | PEA | 35 to 80 |
| 2. | Two Natural FAAH Inhibitors | 0.5 to 40 |
| 3. | Vitamin | 0.01 to 30 |
| 4 | Co-enzyme | 10 to 40 |

General Process for Preparation of the Formulations of the Present Invention

1. Weigh accurately all the ingredients in separate containers.
2. Sift previously weighed PEA, Natural FAAH Inhibitor(s), a diluent (s) and disintegrating agent(s) separately through sieve #40.
3. Mix content of step 2 in rapid mixer granulator (RMG) with impeller of slow speed.
4. Binder solution Preparation: In separate container, weigh a binding agent(s) and Solubilizing agent(s) and dissolve it into solvent(s) and add second natural FAAH Inhibitor(s) (if any) in to same solution.
5. Add binder solution to step 3 in RMG at slow speed of impeller.
6. Sift and dry the obtained granulated wet mass in a Fluid bed dryer at 50° ci 5° C. till the level of dryness (LOD) of the blend is reduced to less than 1.5% w/w.
7. Sift semi dried granules through sieve #20 and sieve #30.
8. Sift previously weighed Lubricant(s) or Glidant(s) separately through sieve #40 and mix with Step-7.
9. Fill and seal the blend with HPMC capsule shells.
10. Transfer the filled capsules into the hopper of polishing and visual inspection machine to remove the debris of powder sticking with the capsule shells.

EXAMPLES

It is understood that the foregoing examples are merely illustrative of the present invention. Certain modifications of the articles and/or methods employed may be made and still achieve the objectives of the invention. Such modifications are contemplated within the scope of the claimed invention.

Example 1

| S. No | Ingredients | Std. Qty. mg/unit | % w/w |
|---|---|---|---|
| | Intragranular Ingredients | | |
| 1 | Micronized PEA | 300 | 66.67 |
| 2 | Natural FAAH Inhibitor (Daidzein) | 50 | 11.11 |
| 3 | MCC pH 101 | 45.5 | 10.11 |
| 4 | Croscarmellose Sodium | 15 | 3.33 |
| | Binder Solution | | |
| 5 | PVP K-30 | 5 | 1.11 |
| 6 | Polysorbate 80 | 10 | 2.22 |
| 7 | IPA | QS | |
| 8 | Water | QS | |
| | Extragranular Ingredients | | |
| 9 | Magnesium Stearate | 10 | 2.22 |
| 10 | Talc | 4 | 0.89 |
| 11 | Zinc Stearate | 6 | 1.33 |
| 12 | Colloidal silicon dioxide | 4.5 | 1.00 |
| | Average Wt. | 450 | 100.00 |

Example 2

| S. No | Ingredients | Std. Qty. mg/unit | % w/w |
|---|---|---|---|
| | Intragranular Ingredients | | |
| 1 | Micronized PEA | 300 | 60.00 |
| 2 | Natural FAAH Inhibitor (Myricetin) | 100 | 20.00 |
| 3 | Lactose Monohydrate | 45.5 | 9.10 |
| 4 | Crospovidone | 15 | 3.00 |
| | Binder Solution | | |
| 5 | Hypromellose | 5 | 1.00 |
| 6 | Polysorbate 80 | 10 | 2.00 |
| 7 | IPA | QS | |
| 8 | Water | QS | |

Example 2 -continued

| S. No | Ingredients | Std. Qty. mg/unit | % w/w |
|---|---|---|---|
| | Extragranular Ingredients | | |
| 9 | Magnesium Stearate | 10 | 2.00 |
| 10 | Talc | 4 | 0.80 |
| 11 | Zinc Stearate | 6 | 1.20 |
| 12 | Colloidal silicon dioxide | 4.5 | 0.90 |
| | Average Wt. | 500 | 100.00 |

Example 3

| S. No | Ingredients | Std. Qty. mg/unit | % w/w |
|---|---|---|---|
| | Intragranular Ingredients | | |
| 1 | Micronized PEA | 300 | 66.67 |
| 2 | Natural FAAH Inhibitor (Isorhamnetin) | 50 | 11.11 |
| 3 | MCC pH 102 | 45.5 | 10.11 |
| 4 | Croscarmellose Sodium | 15 | 3.33 |
| | Binder Solution | | |
| 5 | PVP K-30 | 5 | 1.11 |
| 6 | Sodium Lauryl Sulfate | 10 | 2.22 |
| 7 | IPA | QS | |
| 8 | Water | QS | |
| | Extragranular Ingredients | | |
| 9 | Magnesium Stearate | 10 | 2.22 |
| 10 | Talc | 4 | 0.89 |
| 11 | Zinc Stearate | 6 | 1.33 |
| 12 | Colloidal silicon dioxide | 4.5 | 1.00 |
| | Average Wt. | 450 | 100.00 |

Example 4

| S. No | Ingredients | Std. Qty. mg/unit | % w/w |
|---|---|---|---|
| | Intragranular Ingredients | | |
| 1 | Micronized PEA | 300 | 60.00 |
| 2 | Natural FAAH Inhibitor (Kaempferol) | 100 | 20.00 |
| 3 | Mannitol | 45.5 | 9.10 |
| 4 | Sodium starch glycolate | 15 | 3.00 |
| | Binder Solution | | |
| 5 | PVP K-30 | 5 | 1.00 |
| 6 | Polysorbate 80 | 10 | 2.00 |
| 7 | IPA | QS | |
| 8 | Water | QS | |
| | Extragranular Ingredients | | |
| 9 | Magnesium Stearate | 10 | 2.00 |
| 10 | Talc | 4 | 0.80 |
| 11 | Zinc Stearate | 6 | 1.20 |
| 12 | Colloidal silicon dioxide | 4.5 | 0.90 |
| | Average Wt. | 500 | 100.00 |

Example 5

| S. No | Ingredients | Std. Qty. mg/unit | % w/w |
|---|---|---|---|
| | Intragranular Ingredients | | |
| 1 | Micronized PEA | 300 | 46.15 |
| 2 | Natural FAAH Inhibitor (Pristimerin) | 250 | 38.46 |
| 3 | MCC pH 102 | 45.5 | 7.00 |
| 4 | Croscarmellose Sodium | 15 | 2.31 |
| | Binder Solution | | |
| 5 | Hypromellose | 5 | 0.77 |
| 6 | Polysorbate 80 | 10 | 1.54 |
| 7 | IPA | QS | |
| 8 | Water | QS | |
| | Extragranular Ingredients | | |
| 9 | Magnesium Stearate | 10 | 1.54 |
| 10 | Talc | 4 | 0.62 |
| 11 | Zinc Stearate | 6 | 0.92 |
| 12 | Colloidal silicon dioxide | 4.5 | 0.69 |
| | Average Wt. | 650 | 100.00 |

Example 6

| S. No | Ingredients | Std. Qty. mg/unit | % w/w |
|---|---|---|---|
| | Intragranular Ingredients | | |
| 1 | Micronized PEA | 300 | 60.00 |
| 2 | Natural FAAH Inhibitor (Biochanin) | 100 | 20.00 |
| 3 | Lactose Monohydrate | 45.5 | 9.10 |
| 4 | Crospovidone | 15 | 3.00 |
| | Binder Solution | | |
| 5 | PVP K-30 | 5 | 1.00 |
| 6 | Sodium lauryl sulfate | 10 | 2.00 |
| 7 | IPA | QS | |
| 8 | Water | QS | |
| | Extragranular Ingredients | | |
| 9 | Magnesium Stearate | 10 | 2.00 |
| 10 | Talc | 4 | 0.80 |
| 11 | Zinc Stearate | 6 | 1.20 |
| 12 | Colloidal silicon dioxide | 4.5 | 0.90 |
| | Average Wt. | 500 | 100.00 |

Example 7

| S. No | Ingredients | Std. Qty. mg/unit | % w/w |
|---|---|---|---|
| | Intragranular Ingredients | | |
| 1 | Micronized PEA | 300 | 75.0 |
| 2 | Natural FAAH Inhibitor (Genistein) | 4 | 1.0 |
| 3 | MCC pH 101 | 41.5 | 10.38 |
| 4 | Croscarmellose Sodium | 15 | 3.75 |
| | Binder Solution | | |
| 5 | PVP K-30 | 5 | 1.25 |
| 6 | Polysorbate 80 | 10 | 2.50 |
| 7 | IPA | QS | |
| 8 | Water | QS | |

Example 7 -continued

| S. No | Ingredients | Std. Qty. mg/unit | % w/w |
|---|---|---|---|
| | Extragranular Ingredients | | |
| 9 | Magnesium Stearate | 10 | 2.50 |
| 10 | Talc | 4 | 1.0 |
| 11 | Zinc Stearate | 6 | 1.50 |
| 12 | Colloidal silicon dioxide | 4.5 | 1.13 |
| | Average Wt. | 400 | 100.00 |

Example 8

| S. No | Ingredients | Std. Qty. mg/unit | % w/w |
|---|---|---|---|
| | Intragranular Ingredients | | |
| 1 | Micronized PEA | 300 | 66.67 |
| 2 | Natural FAAH Inhibitor (Daidzein) | 50 | 11.11 |
| 3 | MCC pH 101 | 41.5 | 9.22 |
| 4 | Croscarmellose Sodium | 15 | 3.33 |
| | Binder Solution | | |
| 5 | PVP K-30 | 5 | 1.11 |
| 6 | Polysorbate 80 | 10 | 2.22 |
| 7 | Natural FAAH Inhibitor (Genistein) | 4 | 0.89 |
| 8 | IPA | QS | |
| 9 | Water | QS | |
| | Extragranular Ingredients | | |
| 10 | Magnesium Stearate | 10 | 2.22 |
| 11 | Talc | 4 | 0.89 |
| 12 | Zinc Stearate | 6 | 1.33 |
| 13 | Colloidal silicon dioxide | 4.5 | 1.00 |
| | Average Wt. | 450 | 100.00 |

Example 9

| S. No | Ingredients | Std. Qty. mg/unit | % w/w |
|---|---|---|---|
| | Intragranular Ingredients | | |
| 1 | Micronized PEA | 300 | 54.55 |
| 2 | Natural FAAH Inhibitor (Myricetin) | 100 | 18.18 |
| 3 | Natural FAAH Inhibitor (Isorhamnetin) | 50 | 9.09 |
| 4 | Dicalcium Phosphate | 45.5 | 8.27 |
| 5 | Sodium starch glycolate | 15 | 2.73 |
| | Binder Solution | | |
| 6 | Hypromellose | 5 | 0.91 |
| 7 | Polysorbate 80 | 10 | 1.82 |
| 8 | IPA | QS | |
| 9 | Water | QS | |
| | Extragranular Ingredients | | |
| 10 | Magnesium Stearate | 10 | 1.82 |
| 11 | Talc | 4 | 0.73 |
| 12 | Zinc Stearate | 6 | 1.09 |
| 13 | Colloidal silicon dioxide | 4.5 | 0.82 |
| | Average Wt. | 550 | 100.00 |

Example 10

| S. No | Ingredients | Std. Qty. mg/unit | % w/w |
|---|---|---|---|
| | Intragranular Ingredients | | |
| 1 | Micronized PEA | 300 | 54.55 |
| 2 | Natural FAAH Inhibitor (Kaempferol) | 100 | 18.18 |
| 3 | Natural FAAH Inhibitor (Pristimerin) | 50 | 9.09 |
| 4 | Dicalcium Phosphate | 45.5 | 8.27 |
| 5 | Croscarmellose Sodium | 15 | 2.73 |
| | Binder Solution | | |
| 6 | PVP K-30 | 5 | 0.91 |
| 7 | Polysorbate 80 | 10 | 1.82 |
| 8 | IPA | QS | |
| 9 | Water | QS | |
| | Extragranular Ingredients | | |
| 10 | Magnesium Stearate | 10 | 1.82 |
| 11 | Talc | 4 | 0.73 |
| 12 | Zinc Stearate | 6 | 1.09 |
| 13 | Colloidal silicon dioxide | 4.5 | 0.82 |
| | Average Wt. | 550 | 100.00 |

Example 11

| S. No | Ingredients | Std. Qty. mg/unit | % w/w |
|---|---|---|---|
| | Intragranular Ingredients | | |
| 1 | Micronized PEA | 300 | 60.0 |
| 2 | Natural FAAH Inhibitor (Biochanin) | 100 | 20.0 |
| 3 | Natural FAAH Inhibitor (Genistein) | 4 | 0.80 |
| 4 | Mannitol | 41.5 | 8.30 |
| 5 | Sodium starch glycolate | 15 | 3.0 |
| | Binder Solution | | |
| 6 | PVP K-30 | 5 | 1.0 |
| 7 | Sodium lauryl sulfate | 10 | 2.0 |
| 8 | IPA | QS | |
| 9 | Water | QS | |
| | Extragranular Ingredients | | |
| 10 | Magnesium Stearate | 10 | 2.0 |
| 11 | Talc | 4 | 0.80 |
| 12 | Zinc Stearate | 6 | 1.20 |
| 13 | Colloidal silicon dioxide | 4.5 | 0.90 |
| | Average Wt. | 500 | 100.00 |

Example 12

| S. No | Ingredients | Std. Qty. mg/unit | % w/w |
|---|---|---|---|
| | Intragranular Ingredients | | |
| 1 | Micronized PEA | 300 | 66.67 |
| 2 | Natural FAAH Inhibitor (Daidzein) | 50 | 11.11 |
| 3 | Mannitol | 41.4 | 9.20 |
| 4 | Croscarmellose Sodium | 15 | 3.33 |
| | Binder Solution | | |
| 5 | PVP K-30 | 5 | 1.11 |
| 6 | Polysorbate 80 | 10 | 2.22 |
| 7 | Natural FAAH Inhibitor (Genistein) | 4 | 0.89 |
| 8 | Vitamin (Methylcobalamin) | 0.1 | 0.02 |
| 9 | IPA | QS | |
| 10 | Water | QS | |

Example 12

| S. No | Ingredients | Std. Qty. mg/unit | % w/w |
|---|---|---|---|
| | Extragranular Ingredients | | |
| 11 | Magnesium Stearate | 10 | 2.22 |
| 12 | Talc | 4 | 0.89 |
| 13 | Zinc Stearate | 6 | 1.33 |
| 14 | Colloidal silicon dioxide | 4.5 | 1.00 |
| | Average Wt. | 450 | 100.00 |

Example 13

| S. No | Ingredients | Std. Qty. mg/unit | % w/w |
|---|---|---|---|
| | Intragranular Ingredients | | |
| 1 | Micronized PEA | 300 | 66.67 |
| 2 | Natural FAAH Inhibitor (Daidzein) | 50 | 11.11 |
| 3 | MCC pH 101 | 37.5 | 8.33 |
| 4 | Croscarmellose Sodium | 15 | 3.33 |
| | Binder Solution | | |
| 5 | Hypromellose | 5 | 1.11 |
| 6 | Polysorbate 80 | 10 | 2.22 |
| 7 | Natural FAAH Inhibitor (Genistein) | 4 | 0.89 |
| 8 | Vitamin (Cyanocobalamin) | 4 | 0.89 |
| 9 | IPA | QS | |
| 10 | Water | QS | |
| | Extragranular Ingredients | | |
| 11 | Magnesium Stearate | 10 | 2.22 |
| 12 | Talc | 4 | 0.89 |
| 13 | Zinc Stearate | 6 | 1.33 |
| 14 | Colloidal silicon dioxide | 4.5 | 1.00 |
| | Average Wt. | 450 | 100.00 |

Example 14

| S. No | Ingredients | Std. Qty. mg/unit | % w/w |
|---|---|---|---|
| | Intragranular Ingredients | | |
| 1 | Micronized PEA | 300 | 60.00 |
| 2 | Natural FAAH Inhibitor (Daidzein) | 50 | 10.00 |
| 3 | Coenzyme (Ubidecarenone) | 50 | 10.00 |
| 4 | Lactose Monohydrate | 41.5 | 8.30 |
| 5 | Sodium starch glycolate | 15 | 3.00 |
| | Binder Solution | | |
| 6 | PVP K-30 | 5 | 1.00 |
| 7 | Polysorbate 80 | 10 | 2.00 |
| 8 | Natural FAAH Inhibitor (Genistein) | 4 | 0.80 |
| 9 | IPA | QS | |
| 10 | Water | QS | |
| | Extragranular Ingredients | | |
| 11 | Magnesium Stearate | 10 | 2.00 |
| 12 | Talc | 4 | 0.80 |
| 13 | Zinc Stearate | 6 | 1.20 |
| 14 | Colloidal silicon dioxide | 4.5 | 0.90 |
| | Average Wt. | 500 | 100.00 |

Example 15

| S. No | Ingredients | Std. Qty. mg/unit | % w/w |
|---|---|---|---|
| | Intragranular Ingredients | | |
| 1 | Micronized PEA | 300 | 60.00 |
| 2 | Natural FAAH Inhibitor (Daidzein) | 50 | 10.00 |
| 3 | Coenzyme (Thiamine Pyrophosphate) | 50 | 10.00 |
| 4 | MCC pH 101 | 41.5 | 8.30 |
| 5 | Croscarmellose Sodium | 15 | 3.00 |
| | Binder Solution | | |
| 6 | PVP K-30 | 5 | 1.00 |
| 7 | Polysorbate 80 | 10 | 2.00 |
| 8 | Natural FAAH Inhibitor (Genistein) | 4 | 0.80 |
| 9 | IPA | QS | |
| 10 | Water | QS | |
| | Extragranular Ingredients | | |
| 11 | Magnesium Stearate | 10 | 2.00 |
| 12 | Talc | 4 | 0.80 |
| 13 | Zinc Stearate | 6 | 1.20 |
| 14 | Colloidal silicon dioxide | 4.5 | 0.90 |
| | Average Wt. | 500 | 100.00 |

Example 16

| S. No | Ingredients | Std. Qty. mg/unit | % w/w |
|---|---|---|---|
| | Intragranular Ingredients | | |
| 1 | Micronized PEA | 600 | 80 |
| 2 | Natural FAAH Inhibitor (Daidzein) | 50 | 6.67 |
| 3 | MCC pH 101 | 46.5 | 6.20 |
| 4 | Croscarmellose Sodium | 10 | 1.33 |
| | Binder Solution | | |
| 5 | Natural FAAH Inhibitor (Genistein) | 4 | 0.53 |
| 6 | PVP K-30 | 5 | 0.67 |
| 7 | Polysorbate 80 | 10 | 1.33 |
| 8 | IPA | QS | |
| 9 | Water | QS | |
| | Extragranular Ingredients | | |
| 10 | Magnesium Stearate | 10 | 1.33 |
| 11 | Talc | 4 | 0.53 |
| 12 | Zinc Stearate | 6 | 0.80 |
| 13 | Colloidal silicon dioxide | 4.5 | 0.60 |
| | Average Wt. | 750 | 100.00 |

Example 17

| S. No | Ingredients | Std. Qty. mg/unit | % w/w |
|---|---|---|---|
| | Intragranular Ingredients | | |
| 1 | Micronized PEA | 150 | 35.71 |
| 2 | Natural FAAH Inhibitor (Daidzein) | 75 | 17.86 |
| 3 | MCC pH 101 | 70.5 | 16.79 |
| 4 | Croscarmellose Sodium | 10 | 2.38 |
| | Binder Solution | | |
| 5 | Natural FAAH Inhibitor (Genistein) | 75 | 17.86 |
| 6 | PVP K-30 | 5 | 1.19 |
| 7 | Polysorbate 80 | 10 | 2.38 |
| 8 | IPA | QS | |
| 9 | Water | QS | |

Example 17

| S. No | Ingredients | Std. Qty. mg/unit | % w/w |
|---|---|---|---|
| | Extragranular Ingredients | | |
| 11 | Magnesium Stearate | 10 | 2.38 |
| 12 | Talc | 4 | 0.95 |
| 13 | Zinc Stearate | 6 | 1.43 |
| 14 | Colloidal silicon dioxide | 4.5 | 1.07 |
| | Average Wt. | 420 | 100 |

Stability Study

Example 18—Stability and dissolution study of formulation of Example 1 Stability Condition: ACCELERATED STABILITY TESTING: 40° C., 75% RH

| | | | Duration of Study | | | |
|---|---|---|---|---|---|---|
| S. No | TEST | Specification | Initial | 1 Month | 3 Months | 6 Months |
| 1.0 | Description | White to off white colored granular powder filled in hard HPMC base capsule having red caps and red body. | Complies | Complies | Complies | Complies |
| 2.0 | Average weight of capsules | 550 ± 7.5% | 551.2 mg | 559.3 mg | 551.4 mg | 552.6 mg |
| 3.0 | Net fill content | 450 ± 7.5% | 447.3 mg | 448.1 mg | 450.9 mg | 451.7 mg |
| 4.0 | Disintegration time | Not More Than 30 minutes | 2-4 minutes | 4-5 minutes | 4-5 minutes | 4-5 minutes |
| 5.0 | Assay | | | | | |
| 5.1 | Assay of PEA | Between 90.0% and 110.0% of LC | 99.1% | 100.7% | 101.3% | 99.5% |
| 5.2 | Assay of Daidzein | Between 90.0% and 110.0% of LC | 101.5% | 101.3% | 100.1% | 98.6% |
| 6.0 | Dissolution (60 minutes) | | | | | |
| 6.1 | Dissolution of PEA | Not Less than 70% in 60 minutes | 92.1% | 95.1% | 93.3% | 91.3% |
| 6.2 | Dissolution of Daidzein | Not Less than 70% in 60 minutes | 89.6% | 90.6% | 89.1% | 92.2% |

Example 19—Stability and dissolution study of formulation of Example 7 Stability Condition: ACCELERATED STABILITY TESTING: 40° C., 75% RH

| | | | Duration of Study | | | |
|---|---|---|---|---|---|---|
| S. No | TEST | Specification | Initial | 1 Month | 3 Months | 6 Months |
| 1.0 | Description | White to off white colored granular powder filled in hard HPMC base capsule having red caps and red body. | Complies | Complies | Complies | Complies |
| 2.0 | Average weight of capsules | 500 ± 7.5% | 503.5 mg | 505.8 mg | 504.9 mg | 500.9 mg |
| 3.0 | Net fill content | 400 ± 7.5% | 401.9 mg | 403.8 mg | 404.5 mg | 400.5 mg |
| 4.0 | Disintegration time | Not More Than 30 minutes | 1-2 minutes | 2-3 minutes | 2-3 minutes | 2-3 minutes |
| 5.0 | Assay | | | | | |
| 5.1 | Assay of PEA | Between 90.0% and 110.0% of LC | 99.2% | 99.6% | 100.3% | 100.9% |
| 5.3 | Assay of Genistein | Between 90.0% and 110.0% of LC | 95.9% | 98.9% | 98.3% | 99.9% |
| 6.0 | Dissolution (60 minutes) | | | | | |

-continued

| S. No | TEST | Specification | Duration of Study | | | |
|---|---|---|---|---|---|---|
| | | | Initial | 1 Month | 3 Months | 6 Months |
| 6.1 | Dissolution of PEA | Not Less than 70% in 60 minutes | 95.9% | 96.3% | 92.3% | 94.3% |
| 6.3 | Dissolution of Genistein | Not Less than 70% in 60 minutes | 88.1% | 89.9% | 92.3% | 87.6% |

Example 20—Stability and dissolution study of formulation of Example 8 Stability Condition: ACCELERATED STABILITY TESTING: 40° C., 7500 RH

| S. No | TEST | Specification | Duration of Study | | | |
|---|---|---|---|---|---|---|
| | | | Initial | 1 Months | 3 Months | 6 Months |
| 1.0 | Description | White to off white colored granular powder filled in hard HPMC base capsule having red caps and red body. | Complies | Complies | Complies | Complies |
| 2.0 | Average weight of capsules | 550 ± 7.5% | 555.8 mg | 559.6 mg | 555.3 mg | 552.1 mg |
| 3.0 | Net fill content | 450 ± 7.5% | 458.0 mg | 452.4 mg | 459.4 mg | 455.8 mg |
| 4.0 | Disintegration time | Not More Than 30 minutes | 3-4 minutes | 3-4 minutes | 3-4 minutes | 4-6 minutes |
| 5.0 | Assay | | | | | |
| 5.1 | Assay of PEA | Between 90.0% and 110.0% of LC | 106.9% | 107.3% | 106.2% | 108.2% |
| 5.2 | Assay of Daidzein | Between 90.0% and 110.0% of LC | 100.8% | 100.4% | 98.9% | 99.0% |
| 5.3 | Assay of Genistein | Between 90.0% and 110.0% of LC | 95.6% | 96.8% | 94.6% | 96.9% |
| 6.0 | Dissolution (60 minutes) | | | | | |
| 6.1 | Dissolution of PEA | Not Less than 70% in 60 minutes | 99.0% | 91.8% | 100.7% | 100.2% |
| 6.2 | Dissolution of Daidzein | Not Less than 70% in 60 minutes | 88.8% | 85.4% | 94.0% | 94.8% |
| 6.3 | Dissolution of Genistein | Not Less than 70% in 60 minutes | 80.1% | 88.5% | 89.6% | 95.9% |

Example 21—Animal Study—Screening effect of synergistic combination or composition/formulation comprising PEA and other natural ingredients against Oxaliplatin induced peripheral neuropathy in rat.

Test System and Animal Husbandry
  Species: Rat (*Rattus norvegicus*);
  Strain: Wistar; Sex: Male/Female
  No. of animals: 54 Animals (n=6 per group)
  Animal House conditions:
  Lighting: 12/12 hour light-dark cycle
  Temperature: 25±2° C.
  Relative Humidity: 30 to 70%
  Temperature and relative humidity were recorded Thrice daily.

During Experiments, Standard certified rat pellet feed (Manufactured by Keval Sales Corporation, Vadodara) and drinking water treated by reverse osmosis) were provided ad libitum to all animals.

EXPERIMENTAL PROCEDURE: In study fifty-four (54) rats, were divided into total nine (09) groups. Group 1 served as the normal control, Group 2 served as the disease control, Group 3, Group 4 and Group 5 served as component (A, B and C), Group 6, Group 7 and Group 8 served as formulation of test drug, while Group 9 served as the Reference standard group. For these studies, the following combinations were used.

TABLE 1

Table 1: represents various treatments to respective groups.

| S. No. | Group | No. of Animals | Test Drug |
|---|---|---|---|
| 1 | G1 | 6 | Normal Control |
| 2 | G2 | 6 | Disease Control |
| 3 | G3 | 6 | PEA (60 mg/kg, P.O.) |
| 4 | G4 | 6 | DAIDZEIN (10 mg/kg, P.O.) |
| 5 | G5 | 6 | GENISTEIN (0.8 mg/kg, P.O.) |

TABLE 1-continued

Table 1: represents various treatments to respective groups.

| S. No. | Group | No. of Animals | Test Drug |
|---|---|---|---|
| 6 | G6 | 6 | PEA (60 mg/kg, P.O.) + DAIDZEIN (10 mg/kg, P.O. (Example 1) |
| 7 | G7 | 6 | PEA (60 mg/kg, P.O.) + GENISTEIN (0.8 mg/kg, P.O. (Example 7) |
| 8 | G8 | 6 | PEA (60 mg/kg, P.O.) + DAIDZEIN (10 mg/kg, P.O.) + GENISTEIN (0.8 mg/kg, P.O.) (Example 8) |
| 9 | G9 | 6 | Pregabalin (20 mg/kg, P.O.) |

Group-1 received vehicle (0.25% w/v Sodium CMC) orally (p.o.) for three consecutive days (Day 1, 2 & 3). Group-2 to Group-8 received test drugs, while Group 9 received Pregabalin orally (p.o.) on Day-1, Day-2 and Day-3. All treatment groups (Group 2 to 9) were administered with oxaliplatin (12 mg/kg, i.p.) on Day-3 prior to 2 hrs of test drug administration. After 24 hrs of oxaliplatin administration, treated groups as well as the normal control group were assessed using the Cold hyperalgesia method.

Cold Hyperalgesia method (Tail Immersion Test): In the Tail-immersion test, water was maintained at low (0 to 4-C) temperature. The tail of the rat was immersed in cold water and the duration (time in seconds) of tail immersion was recorded, until the tail was withdrawn from water. The cut-off time of 20 seconds was used. The decrease in tail contact time with cold water was indicative pain whereas prolonged contact time was noted as anti-allodynic effect.

TABLE 2

Effect of administration of 'Test Composition/formulation' on Oxaliplatin induced peripheral neuropathy in rats (Cold Hyperalgesia Method)

| Groups Animal Mark | 1 Normal Control | 2 Disease Control | 3 PEA (60 mg/kg) | 4 Daidzein (10 mg/kg) | 5 Genistein (0.8 mg/kg) | 6 PEA (60 mg/kg) + Daidzein (10 mg/kg) | 7 PEA (60 mg/kg) + Genistein (0.8 mg/kg) | 8 PEA (60 mg/kg) + Daidzein (10 mg/kg) + Genistein (0.8 mg/kg) | 9 Pregabalin (20 mg/kg) |
|---|---|---|---|---|---|---|---|---|---|
| 1 | 20.00 | 16.00 | 11.32 | 8.55 | 7.68 | 17.13 | 16.93 | 18.87 | 17.20 |
| 2 | 20.00 | 14.81 | 11.55 | 8.00 | 7.15 | 17.13 | 16.93 | 18.87 | 20.00 |
| 3 | 20.00 | 6.19 | 10.85 | 8.98 | 7.23 | 17.13 | 16.93 | 18.87 | 20.00 |
| 4 | 20.00 | 5.66 | 10.97 | 7.95 | 7.68 | 17.13 | 16.93 | 18.87 | 19.95 |
| 5 | 20.00 | 4.05 | 11.44 | 8.12 | 7.68 | 17.13 | 16.93 | 18.87 | 18.37 |
| 6 | 20.00 | 3.78 | 10.75 | 8.05 | 7.68 | 17.13 | 16.93 | 18.87 | 20.00 |
| AVG (seconds) | 20.00 | 8.42 | 11.15 | 8.28 | 7.52 | 17.13 | 16.93 | 18.87 | 19.25 |
| % | | | 55.73 | 41.38 | 37.58 | 85.65 | 84.65 | 94.35 | 96.27 |

TABLE 3

Effect of administration of 'Test Composition/formulation' on Oxaliplatin induced peripheral neuropathy in rat

| Groups Group Name (Human Effective Dose/Day) | 1 Normal Control | 2 Disease Control | 3 PEA (600 mg) | 4 Daidzein (100 mg) | 5 Genistein (8 mg) | 6 PEA (600 mg) + Daidzein (100 mg) | 7 PEA (600 mg) + Genistein (8 mg) | 8 PEA (600 mg) + Daidzein (100 mg) + Genistein (8 mg) | 9 Pregabalin (200 mg) |
|---|---|---|---|---|---|---|---|---|---|
| Day 0 | 20.00 | 20.00 | 20.00 | 20.00 | 20.00 | 20.00 | 20.00 | 20.00 | 20.00 |
| Day 4 | 20.00 | 8.42 | 11.15 | 8.28 | 7.52 | 17.13 | 16.93 | 18.87 | 19.25 |
| % | | | 55.73 | 41.38 | 37.58 | 85.65 | 84.65 | 94.35 | 96.27 |

RESULT & DISCUSSION: In this study, Oxaliplatin (12 mg/kg) was administered via intraperitoneal injection in rats. After intraperitoneal injection of Oxaliplatin, there was a significant reduction in tail withdrawal latency in the disease control group. In all treatment groups, either alone or in combination, tail withdrawal latency periods were significantly increased compared to the disease control group. This indicates that treatments were effective against peripheral neuralgia induced by oxaliplatin injection. The effect of treatment groups 6-8 was comparable with that of the standard drug pregabalin as shown in Table 2-3.

CONCLUSION: Based on the above experiments, when rats were treated only with PEA, Daidzein, or Genistein (i.e., Groups 3-5), in comparison to PEA+Daidzein, PEA+Genistein, and PEA+Daidzein+Genistein (i.e., Groups 6-8), the latter was found to be more effective in treating Oxaliplatin induced neuropathic pain in rats at defined dose levels While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the res tills arc contemplated in accordance with the objects and practices of the present invention. It is intended, therefore, that the invention be defined by the scope of the claims which follow and that such claims be interpreted as broadly as is reasonable.

We claim:

1. A pharmaceutical composition consisting of:
   a) 66.67% by wt. of Micronized Palmitoylethanolamide (PEA),
   b) 11.11% by wt. of Daidzein,
   c) 0.89% by wt. of Genistein, and
   d) one or more pharmaceutically acceptable excipients,
   wherein a combination of the PEA, Genistein and Daidzein acts synergistically to reduce neuropathic pain.

2. The pharmaceutical composition as claimed in claim 1, wherein the one or more pharmaceutically acceptable excipients is selected from a diluent, disintegrant, binder, solubilizing agent, lubricant, glidant or solvent.

3. The pharmaceutical composition as claimed in claim 2, wherein the diluent ranges from 5% to 20% by wt. of the composition, the disintegrant ranges from 0.5% to 10% by wt. of the composition, the binder ranges from 0.1% to 10% by wt. of the composition, the solubilizing agent ranges from 0.25% to 15% by wt. of the composition, the lubricant ranges from 1.0% to 10% by wt. of the composition, the glidant ranges from 1.0% to 10% by wt. of the composition, or the solvent is quantity sufficient.

4. The pharmaceutical composition as claimed in claim 1, wherein the composition is in the form of a tablet, capsule, sachet, pill, hard capsule filled with liquid or solid, soft capsule, powder, granule, suspension solution or modified release formulation.

* * * * *